(12) United States Patent
Shirai et al.

(10) Patent No.: US 7,841,965 B2
(45) Date of Patent: Nov. 30, 2010

(54) AUDIO-SIGNAL GENERATION DEVICE

(75) Inventors: Katsuya Shirai, Tokyo (JP); Yoichiro Sako, Tokyo (JP); Toshiro Terauchi, Tokyo (JP); Makoto Inoue, Tokyo (JP); Yasushi Miyajima, Kanagawa (JP); Motoyuki Takai, Tokyo (JP); Kenichi Makino, Kanagawa (JP); Masamichi Asukai, Kanagawa (JP); Kosei Yamashita, Kanagawa (JP)

(73) Assignee: Sony Corporation, Tokyo (JP)

( * ) Notice: Subject to any disclaimer, the term of this patent is extended or adjusted under 35 U.S.C. 154(b) by 97 days.

(21) Appl. No.: 11/486,932

(22) Filed: Jul. 14, 2006

(65) Prior Publication Data

US 2007/0027000 A1 Feb. 1, 2007

(30) Foreign Application Priority Data

Jul. 27, 2005 (JP) .............................. 2005-216682

(51) Int. Cl.
*A63B 71/00* (2006.01)
(52) U.S. Cl. ................................ 482/8; 482/1; 482/901
(58) Field of Classification Search .................. 482/1–9, 482/900–902; 434/247
See application file for complete search history.

(56) References Cited

U.S. PATENT DOCUMENTS

| | | | | | |
|---|---|---|---|---|---|
| 4,776,323 | A | * | 10/1988 | Spector | 601/23 |
| 5,137,501 | A | * | 8/1992 | Mertesdorf | 482/57 |
| 5,533,947 | A | * | 7/1996 | Tomlinson et al. | 482/6 |
| 5,738,613 | A | * | 4/1998 | Clayton | 482/47 |
| 5,830,107 | A | * | 11/1998 | Brigliadoro | 482/1 |
| 6,032,530 | A | * | 3/2000 | Hock | 73/379.01 |
| 6,251,048 | B1 | * | 6/2001 | Kaufman | 482/8 |
| 6,293,802 | B1 | * | 9/2001 | Ahlgren | 434/252 |
| 6,447,424 | B1 | * | 9/2002 | Ashby et al. | 482/8 |
| 6,685,480 | B2 | * | 2/2004 | Nishimoto et al. | 434/247 |
| 6,695,694 | B2 | * | 2/2004 | Ishikawa et al. | 463/7 |
| 6,746,247 | B2 | * | 6/2004 | Barton | 434/247 |
| 7,060,008 | B2 | * | 6/2006 | Watterson et al. | 482/54 |
| 7,160,200 | B2 | * | 1/2007 | Grober | 473/234 |
| 2001/0034014 | A1 | * | 10/2001 | Nishimoto et al. | 434/247 |
| 2002/0055383 | A1 | * | 5/2002 | Onda et al. | 463/36 |
| 2005/0148450 | A1 | * | 7/2005 | Huang | 482/147 |
| 2006/0142082 | A1 | * | 6/2006 | Chiang et al. | 463/36 |
| 2007/0149361 | A1 | * | 6/2007 | Jung et al. | 482/8 |
| 2007/0270667 | A1 | * | 11/2007 | Coppi et al. | 600/300 |
| 2008/0139080 | A1 | * | 6/2008 | Zheng | 446/268 |

FOREIGN PATENT DOCUMENTS

| | | |
|---|---|---|
| JP | 55-12452 | 1/1980 |
| JP | 61-953 | 1/1986 |
| JP | 06-054093 U | 7/1994 |

(Continued)

*Primary Examiner*—Glenn Richman
(74) *Attorney, Agent, or Firm*—Wolf, Greenfield & Sacks, PC

(57) ABSTRACT

An audio-signal generation device includes a generation circuit which generates track data and an input unit which receives information input by a user. The generation circuit generates the track data on the basis of information about the user's body, information about an exercise to be done, and information about a characteristic of a track to which the user listens during the exercise that are input via the input unit.

9 Claims, 10 Drawing Sheets

FOREIGN PATENT DOCUMENTS

| | | |
|---|---|---|
| JP | 06-236183 A | 8/1994 |
| JP | 07-325568 A | 12/1995 |
| JP | 9-276348 | 10/1997 |
| JP | 2001-275999 | 10/2001 |
| JP | 2001-299980 | 10/2001 |
| JP | 2001-306071 | 11/2001 |
| JP | 2002-73018 | 3/2002 |
| JP | 2003-125806 A | 5/2003 |
| JP | 2003-177750 | 6/2003 |
| JP | 2003-305146 | 10/2003 |
| JP | 2004-113552 | 4/2004 |
| JP | 2004-216142 | 8/2004 |

* cited by examiner

FIG. 3A

PLEASE INPUT YOUR PROFILE

NAME
AGE         YEAR(S) OLD
HEIGHT      cm
WEIGHT      kg

NAME     Tanaka_Ichirou
AGE      30YEARS OLD
HEIGHT   170cm    WEIGHT   60kg
BMI      20.8
OBESITY INDEX   1
         OK?      YES   NO

PLEASE INPUT INFORMATION
ABOUT EXERCISE YOU ARE
GOING TO DO

TYPE
MODE
SPEED AND
TEMPO
TIME

TYPE             WALKING
MODE             CONSTANT
SPEED AND        5km/h
TEMPO
TIME             30 MINUTES

OK?      YES   NO

WHAT KIND OF TRACK DO YOU PREFER?

TONE

GENRE

TRACK NUMBER

| TONE | BRIGHT AND RHYTHMICAL |
| GENRE | POP |
| TRACK NUMBER | 1 |

OK?  YES  NO

SHOW EXERCISE INFORMATION

| | |
|---|---|
| EXERCISE TIME | 30:00 MINUTES |
| WALK DISTANCE | 2.754km |
| AVERAGE SPEED | 5.00km/h |
| CALORIE CONSUMPTION | 101kcal |
| FAT-BURNING AMOUNT | 13.1g |

WELL DONE!

PREDETERMINED EXERCISE AMOUNT IS NOT ATTAINED THOUGH PREDETERMINED TIME ELAPSES

DO YOU CONTINUE EXERCISE TILL PREDETERMINED EXERCISE AMOUNT IS ATTAINED?

[YES] [NO]

PREDETERMINED EXERCISE AMOUNT IS ATTAINED THOUGH PREDETERMINED TIME DOES NOT ELAPSE

DO YOU CONTINUE EXERCISE?

[YES] [NO]

| TYPE |
|---|
| WALKING |
| JOGGING |
| CYCLING |
| AEROBICS |

FIG. 6B

| MODE |
|---|
| CONSTANT |
| RISE AND FALL |
| REPEAT |
| RANDOM |

FIG. 6C

| SPEED AND TEMPO |
|---|
| 4km/h · 80bpm |
| 6km/h · 100 |
| 8km/h · 120 |
| 10km/h · 130 |
| 12km/h · 140 |
| 16km/h · 150 |

FIG. 6D

| EXERCISE TIME |
|---|
| 10 MINUTES |
| 20 MINUTES |
| 30 MINUTES |
| 45 MINUTES |
| 60 MINUTES |

FIG. 6E

| TONE |
|---|
| SLOWLY |
| GENTLY |
| PEACEFULLY |
| BRIGHTLY |
| LIVELY |
| CHEERFULLY |
| ⋮ |

FIG. 6F

| GENRE |
|---|
| POP |
| ROCK |
| JAZZ |
| HEAVY METAL |
| NURSERY SONG |
| ⋮ |

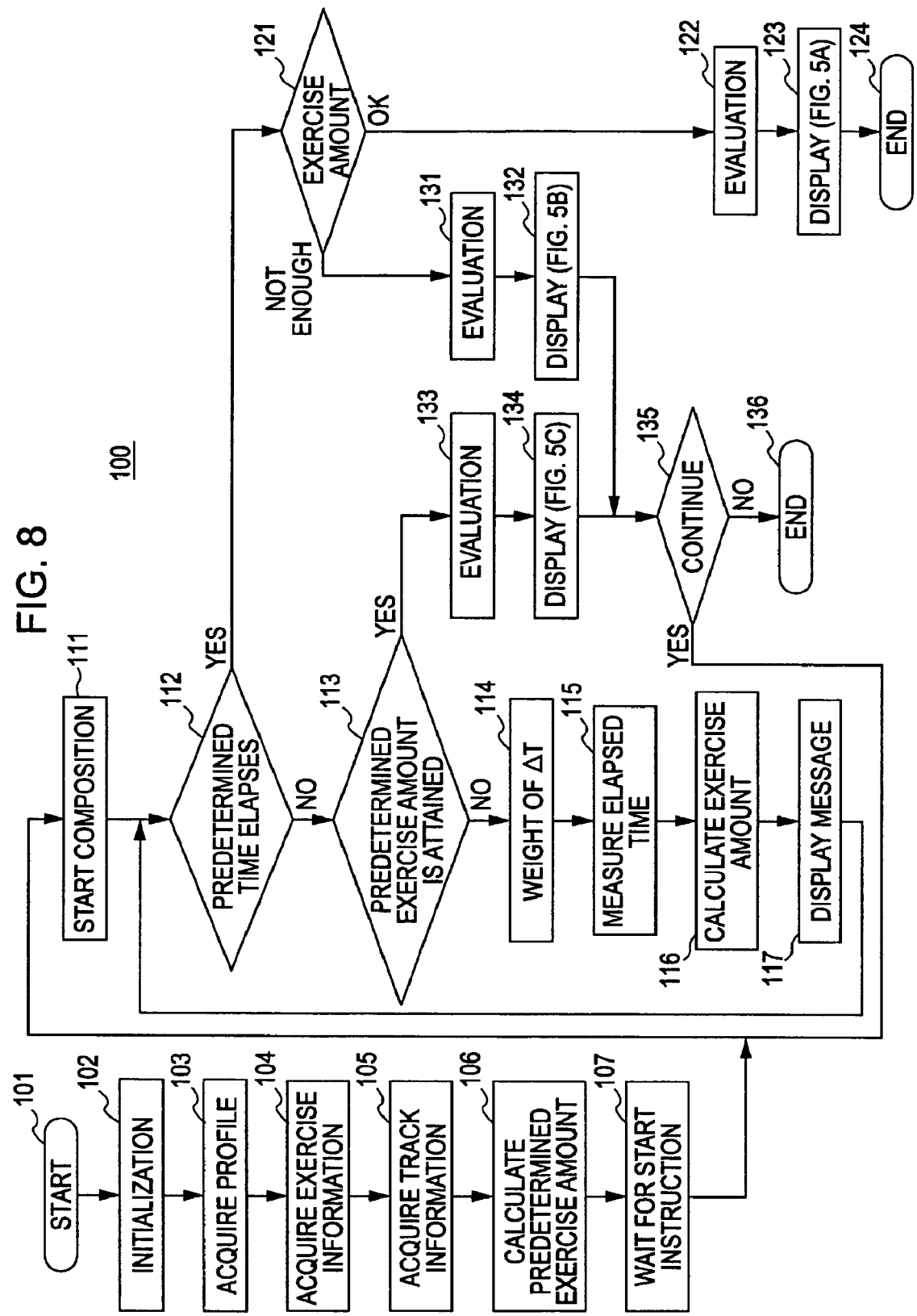

FIG. 9A

RISE AND FALL MODE

| EXERCISE TIME | EXERCISE TEMPO | TRACK GENRE | TONE | TRACK NUMBER |
|---|---|---|---|---|
| FIVE MINUTES | 80 | POP | SLOWLY | 1 |
| TEN MINUTES | 100 | POP | GENTLY | 2 |
| THIRTY MINUTES | 120 | ROCK | MERRILY AND LIVELY | 5 |
| TEN MINUTES | 100 | POP | CALMLY | 2 |
| FIVE MINUTES | 80 | POP | PEACEFULLY | 1 |

FIG. 9B

RANDOM MODE

| EXERCISE TIME | EXERCISE TEMPO | TRACK GENRE | TONE | TRACK NUMBER |
|---|---|---|---|---|
| TEN MINUTES | 80 | POP | SLOWLY | 1 |
| TEN MINUTES | 130 | ROCK | BRIGHTLY | 2 |
| TEN MINUTES | 100 | JAZZ | MERRILY | 3 |
| TEN MINUTES | 150 | HEAVY METAL | VIOLENTLY | 2 |
| FIVE MINUTES | 100 | POP | CALMLY | 1 |
| FIVE MINUTES | 80 | NURSERY SONG | PEACEFULLY | 1 |

FIG. 10

| GENRE | POP |
|---|---|
| INSTRUMENT(S) | GUITAR, BASE, DRUM, KEYBOARD |
| RHYTHM | TWO BEATS, FOUR BEATS, EIGHT BEATS, SIXTEEN BEATS,… |
| CHORD PROGRESSION | MAJOR(C-F-G-C,F-G-C-F,D-A-G-D,…)<br>MINOR(Am-Dm-Em-Am,Dm-Gm-Am-Dm,…)<br>TYPICAL CHORD PROGRESSION<br>(C-G-Am-Em,F-C-F-G,D-A-Bm-F#m-G-D-G-A,…)<br>GENERATE CHORD AT RANDOM |
| PERFORMANCE STYLE | J-POP MANNER, 80'S MANNER, 90'S MANNER…<br>CHORD ONLY, GENERATE CHORD PROGRESSION AT RANDOM, GENERATE MELODY AUTOMATICALLY… |
| PERFORMANCE RULE | ADD BASE NOTE AFTER REPEAT (BASE), ARPEGGIO (GUITAR)<br>EMPHASIZE BASE AND DRUM WHEN EMPHASIZING RHYTHM … |

AUDIO-SIGNAL GENERATION DEVICE

CROSS REFERENCES TO RELATED APPLICATIONS

The present invention contains subject matter related to Japanese Patent Application JP 2005-216682 filed in the Japanese Patent Office on Jul. 27, 2005, the entire contents of which are incorporated herein by reference.

BACKGROUND OF THE INVENTION

1. Field of the Invention

The present invention relates to an audio-signal generation device.

2. Description of the Related Art

In recent years, there has been a growth in the number of people doing exercises including jogging, walking, running, aerobics, and so forth, so as to maintain and/or increase health, diet, and so forth due to increased health consciousness. For achieving a predetermined effect through the above-described exercises, a person should continue exercising over a certain period of time. Therefore, for making the person continue doing an exercise with enjoyment, there have been proposed acoustic-reproduction devices that can aid in motivating the person to do the exercise and making the person continue doing the exercise by using music and that can display information about an effective pace of the exercise.

For example, Japanese Patent Unexamined Application Publication No. 2001-299980 discloses a device which detects information about the tempo of an exercise done by an exerciser, corrects the tempo of reproduced music on the basis of a difference between the pulse rate of the exerciser and a target pulse rate, and guides the exerciser's pulse rate to the target pulse rate.

Japanese Patent Unexamined Application Publication No. 2002-73018 discloses the following technologies and/or device. Namely, when an exerciser does an exercise such as aerobics, the technology and/or device allows for reading track data written on the basis of musical-instrument-digital-interface (MIDI) data from a musical database, and changing and displaying information about the tempo of a selected track according to exercise conditions (a tempo, a change in the tempo with reference to an exercise-progression time) representing a target of the exerciser. Further, Japanese Patent Unexamined Application Publication No. 2001-306071 and Japanese Patent Unexamined Application Publication No. 2003-305146 disclose technologies and/or devices which allow for reading and displaying track data from a musical database provided on a network and/or the Internet according to exercise conditions representing a target of an exerciser.

SUMMARY OF THE INVENTION

However, the device disclosed in Japanese Patent Unexamined Application Publication No. 2001-299980 requires a measuring device specifically designed for measuring the exercise amount and/or pulse rate of the exerciser, so that the entire configuration of the device becomes complicated.

In the case of the device disclosed in Japanese Patent Unexamined Application Publication No. 2002-73018, the device edits a track according the exercise conditions representing the exerciser's target. Therefore, a large-scale system including a synthesizer is required. Further, for reproducing the edited track, data on the edited track is temporarily recorded on a recording medium such as a cassette tape. Thus, the above-described device has poor portability.

Further, each of the devices disclosed in Japanese Patent Unexamined Application Publication No. 2001-306071 and Japanese Patent Unexamined Application Publication No. 2003-305146 has to access a musical database via the Internet, so as to acquire track data, which makes it difficult to operate the device. In the case where the device disclosed in Japanese Patent Unexamined Application Publication No. 2003-305146 is used, an exerciser selects a target track from among many tracks that had been prepared, which makes it difficult for the exerciser to select a track with a tempo preferred by the exerciser.

Accordingly, the present invention has been achieved, so as to provide an audio-signal generation device which solves the above-described problems, has increased portability, and aids in motivating a person to do an exercise including walking, jogging, and so forth, making the person continue doing the exercise, and making the person do the exercise effectively through simple operations.

An audio-signal generation device according to an embodiment of the present invention includes a generation circuit which generates track data and an input unit which receives information input by a user. The generation circuit generates the track data on the basis of information about the user's body, information about an exercise to be done, and information about a characteristic of a track to which the user listens during the exercise that are input via the input unit.

The present invention allows a user to do an exercise including walking, jogging, and so forth to a track with a tone preferred by the user, and continue doing the exercise with enjoyment. Further, if a certain period of time is required, the user can continue doing the exercise.

BRIEF DESCRIPTION OF THE DRAWINGS

FIG. 3A shows an example display image used for inputting information;

FIG. 3B shows an example display image used for confirming the input information;

FIG. 3C shows another example display image used for inputting information;

FIG. 3D shows another example display image used for confirming the input information;

FIG. 4A shows another example display image used for inputting information;

FIG. 4B shows another example display image used for confirming the input information;

FIG. 5A shows an example display image displayed, so as to show a use result;

FIG. 5B shows an example display image displayed, so as to show another use result;

FIG. 5C shows an example display image displayed, so as to show another use result;

FIG. 6A is a display image showing an example input menu and example options of the input menu;

FIG. 6B is a display image showing another example input menu and example options of the input menu;

FIG. 6C is a display image showing another example input menu and example options of the input menu;

FIG. 6D is a display image showing another example input menu and example options of the input menu;

FIG. 6E is a display image showing another example input menu and example options of the input menu;

FIG. 6F is a display image showing another example input menu and example options of the input menu;

FIG. 8 is a flowchart showing another embodiment of the present invention;

FIG. 9A shows example details on the above-described exercise mode shown in FIG. 7B;

FIG. 9B shows example details on the above-described exercise mode shown in FIG. 7D; and FIG. 10 shows example details on a parameter file.

DESCRIPTION OF THE PREFERRED EMBODIMENTS

[1] Example Configuration

[1-1] Example Appearance

Figure 1:
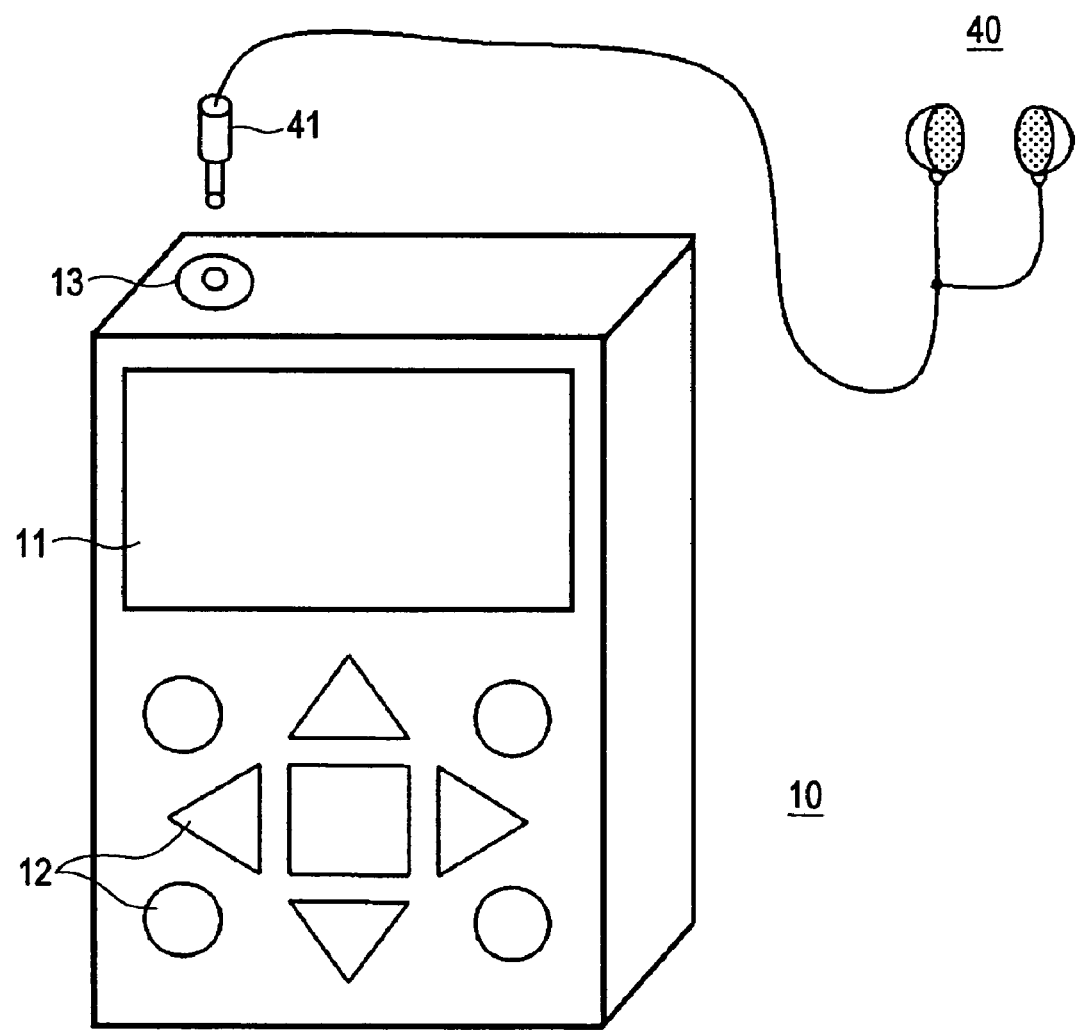
FIG. 1 is a perspective view showing the appearance of a device according to an embodiment of the present invention.

FIG. 1 shows an example appearance of a generation device 10 according to an embodiment of the present invention, the generation device 10 being provided, so as to generate an audio signal. The entire generation device 10 is manufactured, as a substantially-flat parallelepiped in such a size that the generation device 10 can be put into a breast pocket. A liquid-crystal-display (LCD) panel 11 is provided on upper part of the front of the generation device 10. Further, various operation keys 12 including cursor keys (direction keys), an enter key, a cancel key, and so forth are provided on lower part of the front of the generation device 10, as input devices. Further, a headphone jack 13 is provided on a top face of the generation device 10 so that a plug 41 of a pair of headphones (an earphone) 40 can be connected thereto.

Upon receiving various information items and/or condition information items transmitted from a user (an exerciser) via the operation key 12, the generation device 10 automatically composes a track according to the input information items and/or condition information items, where the track has characteristics which will be described later. Then, the generation device 10 transmits an audio signal of the track to the headphones 40. Subsequently, the user can exercise with enjoyment to the track output from the headphones 40.

[1-2] Example Circuit

Figure 2:
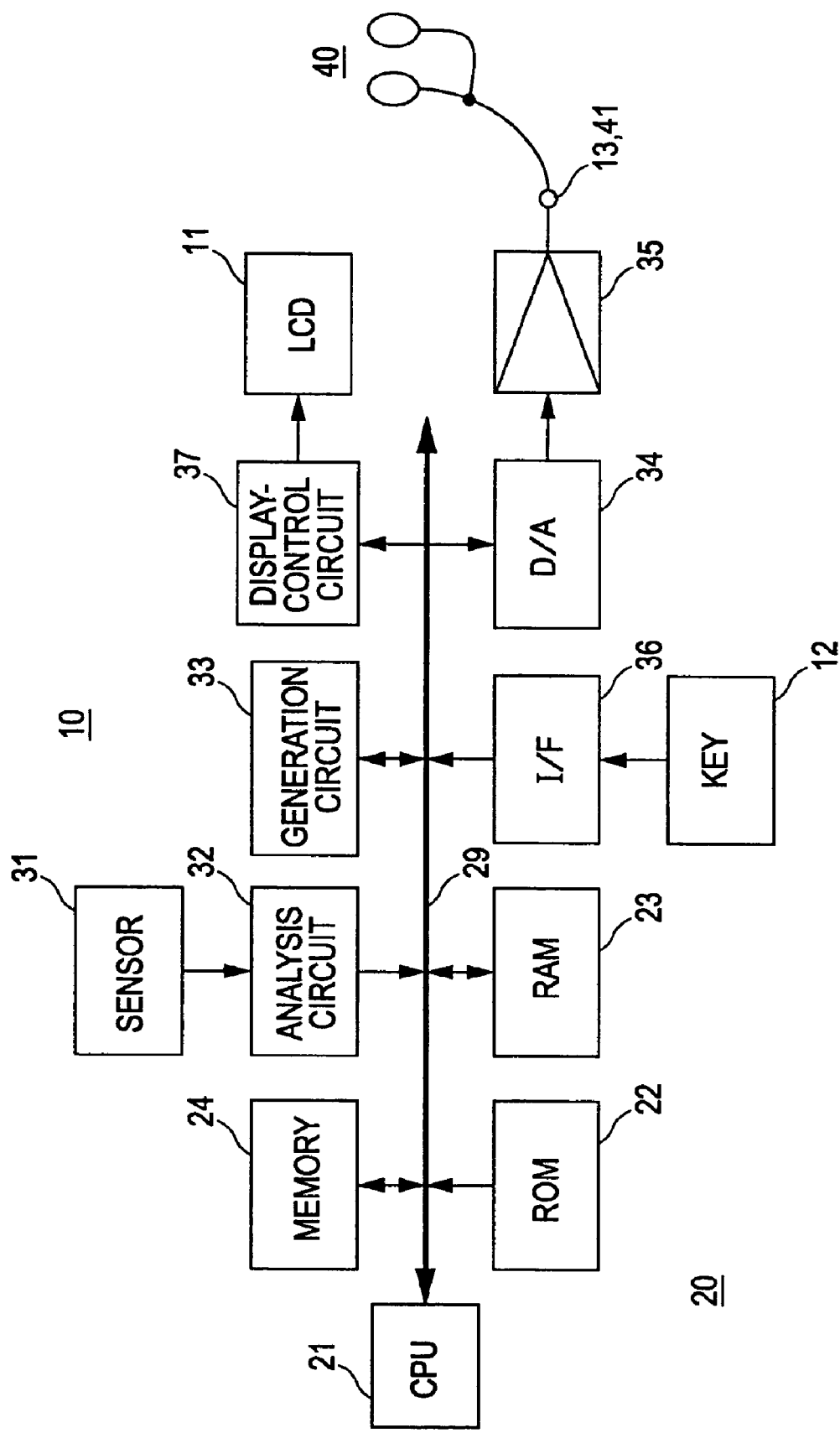
FIG. 2 is a block diagram of a device according to another embodiment of the present invention.

FIG. 2 shows an example circuit configuration of the generation device 10 which generates the audio signal. The generation device 10 has a microcomputer 20 provided, as a system-control circuit. The microcomputer 20 includes a central-processing unit (CPU 21) executing a program, a read-only memory (ROM) 22 storing various programs, a random-access memory (RAM) 23 which is used, as a work area, and a nonvolatile memory 24. Each of the above-described memories 22, 23, and 24 is connected to the CPU 21 via a system bus 29. In that case, the nonvolatile memory 24 is provided, so as to store information about the profile of the exerciser (the user of the generation device 10) and data on the exercise result or the like. A program stored in the ROM 22 will be described later.

Further, the generation device 10 includes an exercise-information sensor 31 and an analysis circuit 32 which analyzes information transmitted from the exercise-information sensor 31. More specifically, the exercise-information sensor 31 detects information about the state of an exercise done by the exerciser. Further, the analysis circuit 32 analyzes the detected information output from the exercise-information sensor 31 and transmits information about the exercise tempo to the microcomputer 20. For example, when the exerciser does walking, the exercise-information sensor 31 detects motions of the exerciser's body and the analysis circuit 32 analyzes the detection result so that a tempo pulse is transmitted to the system bus 29 in synchronization with the walking motion.

Further, the generation device 10 includes a track-data-generation circuit 33. The track-data-generation circuit 33 automatically generates data on a predetermined track according to an instruction transmitted from the CPU 21. In the above-described embodiment, for the sake of simplicity, when the CPU 21 transmits predetermined information, that is, information about the track type, mode, speed and tempo, time, tone, genre, and track number, and an instruction to start composing, the track-data generation circuit 33 generates digital-audio data on a track generated according to the above-described information and transmits the digital-audio data to the system bus 29.

Further, the generation device 10 includes and a digital-to-analog (D/A) converter circuit 34 and an audio amplifier 35. The D/A converter circuit 34 is connected to the system bus 29. Then, the digital-audio data transmitted from the track-data-generation circuit 33 is transmitted to the D/A converter circuit 34 so that the digital-audio data is subjected to D/A conversion and converted into an analog-audio signal. The analog-audio signal is transmitted to the headphone jack 13 via the audio amplifier 35 and transmitted to the headphones 40.

Then, the operation key 12 is connected to the system bus 29 via an interface circuit 36, and a display-control circuit 37 is connected to the system bus 29 and a display signal is obtained. The display signal is transmitted to the LCD panel 11 so that predetermined text including a number and a sign is displayed on the LCD panel 11.

[2] Operations and Usage

Here, in the case where walking is done, as the exercise, the generation device 10 operates and is used, as below. Namely, when a power key provided, as one of the operation keys 12, is pressed down, the power of the generation device 10 is turned on. If the power is turned on for the first time after the generation device 10 was purchased, the generation device 10 enters mode of inputting information about the body of the user (exerciser), that is, information about the user's profile.

Namely, as shown in FIG. 3A, the LCD panel 11 displays a sentence encouraging to input the user's profile and input fields used for inputting information about the name, age, height, and body weight of the user, for example. If the user inputs necessary information by operating the operation key 12, the input result is displayed, and the user is requested to confirm the input result, as shown in FIG. 3B, for example. FIG. 3B shows the case where a body-mass index (BMI) is calculated on the basis of the inputted information about the height and the body weight, and the BMI and an obesity index calculated on the basis of the BMI are displayed, at the same time.

If an instruction to correct the display contents shown in FIG. 3B is transmitted, the screen image returns to the profile-input screen image shown in FIG. 3A so that the profile information can be corrected and/or input again. Then, the confirmation screen image shown in FIG. 3B is displayed. Further, when an instruction to approve the display contents shown in FIG. 3B is transmitted, the mode of inputting information about the user's profile is terminated. At that time, the input information about the user's profile is stored in the nonvolatile memory 24.

Further, when the information about the user's profile had already been stored in the nonvolatile memory 24 at the time where the power of the generation device 10 is turned on, that is to say, when the generation device 10 is used for the at least second time after the generation device 10 was purchased, the input fields used for inputting the name and age of the user are not displayed, the input fields being shown in FIG. 3A, and only the input fields used for inputting information about the height and weight are displayed, and the user is requested to input the information about the height and weight.

Then, following the confirmation display screen shown in FIG. 3B, the generation device 10 enters mode of inputting information about an exercise which will be done. For example, the LCD panel 11 displays input fields used for inputting information about the type, mode, speed and tempo, and time of the exercise, as shown in FIG. 3C. In that case, the exercise-type information may be shown, as "walking", "jogging", "aerobics", and so forth, as shown in FIG. 6A, for example. When the cursor key of the operation keys 12 is pressed down, the above-described exercise names are shown in the input fields in sequence. If the name of a target exercise is displayed, the enter key of the operation keys 12 is pressed down.

Further, exercise mode indicates details on the speed and tempo of an exercise, as shown in FIGS. 6B, 7A, 7B, 7C, and 7D. For example, mode of making the speed and tempo constant from the first till the end (FIG. 7A), mode of making the speed and tempo rise and/or fall at a constant rate (FIG. 7B), mode of making the speed and tempo change periodically (FIG. 7C), and mode of making the speed and tempo change at random (FIG. 7D) are provided. Then, the mode selection is performed, as is the case with the exercise type. Further, the values of the speed and tempo, and a time of the exercise are selected from among values shown in FIGS. 6C and 6D, as is the case with the mode selection and the exercise type.

Further, when the user inputs necessary information on the input screen image shown in FIG. 3C, the input result is displayed, as shown in FIG. 3D, for example, and the user is requested to confirm the input result. If the user instructs to correct the display contents shown in FIG. 3D, the screen image returns to the input screen shown in FIG. 3C so that information about an exercise the user is going to do can be corrected. Then, the screen image advances to a confirmation screen image shown in FIG. 3D. Further, if the user approves the display contents shown in FIG. 3D, the mode of inputting information relating to the exercise the user is going to do is terminated. At that time, the input information about the exercise the user going to do is stored in the nonvolatile memory 24.

Then, following the confirmation screen image shown in FIG. 3D, the generation device 10 enters mode of inputting information about the characteristics of at least one track to which the user listens while he does the exercise. For example, the LCD panel 11 shows input fields used for inputting information about the tone, genre, number of the track, as shown in FIG. 4A. In that case, the tone information indicates the tone of a track composed by a track-data generation circuit 33. For example, information items indicating "slowly", "gently", "peacefully", "brightly", and "lively" are provided, as shown in FIG. 6E so that the user selects a desired information item from among the above-described information items. Further, the genre information denotes the genre of the track composed by the track-data generation circuit 33. For example, information items indicating "pop", "rock", "jazz", "heavy metal" and so forth are provided, as shown in FIG. 6F so that the user selects a desired information item from among the above-described information items. Further, the track-number information indicates the number of at least one track composed while the user does one walking (one exercise).

Then, when the user inputs necessary information, the input result is displayed, as shown in FIG. 4B, for example, and the user is requested to confirm the input result. If the user instructs to correct the display contents shown in FIG. 4B, the screen image returns to the input screen shown in FIG. 4A so that a request made for a track which will be composed can be corrected. Then, the screen image advances to the confirmation screen image shown in FIG. 4B. Further, if the user transmits an instruction to approve the display contents shown in FIG. 4B, the mode of inputting the request made for the track to which the user listens while he does the exercise is terminated. At that time, the input information about the request made for the track is stored in the nonvolatile memory 24.

When the enter key of the operation keys 12 is pressed down after the above-described information is input, the track-data generation circuit 33 starts generating digital-audio data on the track automatically, and the digital-audio data is transmitted to the D/A converter circuit 24 so that the track is output from the headphones 40. Then, the user performs an exercise such as walking at the tempo of the track output from the headphones 40. Hereinafter, the description will be given on the premise that the user does walking.

In that case, the tempo of the track output from the headphones 40 is determined according to the tempo information input on the input screen image shown in FIG. 3C. Predetermined mode is selected from among the modes shown in FIGS. 6A, 6B, 6C, and 6D according to information input on the input screen image shown in FIG. 3C. Further, the tone and genre of the current track satisfies predetermined conditions, that is, the information input on the input screen image shown in FIG. 4A.

Subsequently, the details on the track output from the headphones 40 respond to the request made by the user. Therefore, the user can enjoy walking during an exercise time period determined according to the information input on the input screen image shown in FIG. 3C.

While the user does walking, the exercise-information sensor 31 detects the motion of the user's body and the analysis circuit 32 outputs a pulse in synchronization with the user's walking. Subsequently, the microcomputer 20 can obtain information about the walking state of the user by monitoring the pulse. The walking-state information includes information about the speed (tempo), an actual walking time, and so forth.

Therefore, while the user does walking, the tempo of the pulse output from the analysis circuit 32 is detected. More specifically, the difference between the walking tempo and the tempo of the automatically composed track is detected, and the following messages are displayed on the LCD panel 11 according to the detection result, for example.

Namely, (1) When the tempo of walking agrees with the track tempo while the user walks.

"You walk at appropriate pace. Please continue walking At this speed."

(2) When the tempo of walking is slower than the track tempo while the user walks.

"You walk too slowly. Please walk at quicker tempo."

(3) When the tempo of walking is faster than the track tempo while the user walks.

"You walk too fast. Please walk at slower tempo."

(4) When the user does not start walking even though track performance is started.

"Please start walking!"

(5) When the user stops walking.

"Please continue walking!"

Further, while the user walks, a time which had elapsed and a walking amount which had been accumulated since the user started walking are measured.

Then, when an exercise time determined according to the information input on the input screen image shown in FIG. 3C elapses, the track-data generation circuit 33 finishes generating the track data and the headphones 40 stop outputting the track. At that time, exercise information is calculated on the basis of the information input on the input screen image shown in FIG. 3C and a result of monitoring the pulse output from the analysis circuit 32. The exercise information includes information about the execution time, distance, average speed, calorie consumption, fat-burning amount, and so forth of the walking. The above-described exercise information is displayed on the LCD panel 11, as shown in FIG. 5A, for example.

However, the above-described exercise information can be displayed, as shown in FIG. 5A, only when the user does walking in an appropriate manner according to the information input on the input screen image shown in FIG. 3C. That is to say, when the user takes time off during walking and/or walks at slower tempo, for example, a predetermined exercise amount (the exercise amount calculated on the basis of the information input on the input screen image shown in FIG. 3C) is not attained even though the time determined according to the information input on the input screen image shown in FIG. 3C elapses.

In that case, therefore, predetermined sentences are displayed on the LCD panel 11, so as to inform the user that the predetermined exercise amount is not attained and ask the user whether or not the user continues walking till the predetermined exercise amount is attained.

On the contrary, if the tempo of walking is quickened, the predetermined exercise amount is attained before the time determined according to the information input on the input screen image shown in FIG. 3C elapses. In that case, therefore, predetermined sentences are displayed on the LCD panel 11, so as to inform the user that the predetermined exercise amount is attained and ask the user whether or not the user continues walking till the predetermined time elapses.

Then, when information indicating that the user continues walking is input on the inquiry screen image shown in FIG. 5B and/or FIG. 5C, the track-data generation and the walking monitoring is started again. If the predetermined exercise amount is attained and/or the exercise time corresponding to the input exercise-time information elapses, the track generation is finished, and the exercise result is displayed, as is the case with FIG. 5A, and the entire processing is finished.

Further, when an instruction to finish walking is input on the inquiry screen image shown in FIG. 5B and/or FIG. 5C, information about the exercise amount and the exercise time that had been attained until then is displayed, as is the case with FIG. 5A, and the entire processing is finished.

Thus, according to the generation device 10, the user can walk to the track, where the tempo of the track used for the walking is set by the user, and the tone and/or genre of the track is determined according to the preference of the user.

Subsequently, over a certain period of time, the user can continue walking with enjoyment. Further, since the track used for walking is automatically generated, the user does not have to collect favorite tracks from a compact disc (CD) or the like without concern for copyrights or the like.

[3] Example Processing Routine

In FIG. 8, reference numeral 100 denotes an example routine provided, so as to execute the processing described with reference to FIGS. 3A to 7D. The routine 100 is prepared in the ROM 22 and executed by the CPU 21. FIG. 8 shows part of the routine 100, the part being related to the present invention.

Namely, when the power of the generation device 10 is turned on, the CPU 21 starts performing processing at step 101 of the routine 100. Then, each of the above-described units is initialized, at step 102, and the generation device 10 enters the mode of inputting information about the exerciser's profile, which was described with reference to FIGS. 3A and 3B, at step 103. After inputting and confirming the exerciser's profile, the corresponding data is stored in the nonvolatile memory 24.

Then, at step 104, the generation device 10 enters the mode of inputting information about an exercise the user is going to do, which was described with reference to FIGS. 3C and 3D. After inputting and confirming necessary information relating to the exercise, the corresponding data is stored into the nonvolatile memory 24. Then, the processing advances to step 105 where the generation device 10 enters the mode of inputting information about the track used while the exercise is done, which was described with reference to FIGS. 4A and 4B.

Then, after inputting and confirming the necessary information relating to the track, the corresponding data is stored in the nonvolatile memory 24. After that, at step 106, a predetermined exercise amount is calculated on the basis of the data which is input at step 104. Then, at step 107, the generation device 10 waits until an instruction to start automatic track-composition is issued.

Then, when the enter key of the operation keys 12 is pressed down, the processing advances to step 111 and the instruction to start automatic track-composition is transmitted to the track-data generation circuit 33. At that time, the information which is input and stored in the nonvolatile memory 24 at steps 104 and 105, namely, the information about the type, mode, speed and tempo, time, tone, genre, and number of the track is transmitted to the track-data generation circuit 33.

Therefore, the automatic track-data generation is started at step 111 and the track data is generated according to a user's request acquired, at step 105. Since the track is output from the headphones 40, the exerciser (the user of the generation device 10) starts walking to the track.

On the other hand, the processing executed by the CPU 21 advances from step 111 to step 112 where it is determined whether or not the time corresponding to the exercise-time information acquired at step 104 had elapsed since the processing corresponding to step 111 was performed. Since the time had not elapsed in the above-described embodiment, the processing advances from step 112 to step 113 where it is determined whether or not the amount of the exercise done by the exerciser had reached the predetermined exercise amount calculated at step 106. In that case, the amount of the exercise done by the exerciser had not reached the predetermined exercise amount. Therefore, the processing advances from step 113 to step 114.

At step 114, the generation device 10 waits over a predetermined unit time period $\Delta T$ (e.g., $\Delta T$=one minute). Then, at step 115, a counter indicating a time which had elapsed since the processing corresponding to step 111 was performed, that is, a counter indicating a time which had elapsed since the track output was started is incremented. At step 112, it is determined whether or not the time corresponding to the exercise-time information acquired at step 104 had elapsed on the basis of the elapsed time indicated by the counter.

Then, the processing advances to step 116 where the exercise amount which had been accumulated since the exercise was started is calculated according to a method which will be described later. At step 117, the state of the exercise done by the exerciser is determined on the basis of the cycle of the pulse output from the analysis circuit 32 and the elapsed-time information acquired at step 115, and the message corresponding to the determination result is selected from among the messages (1) to (5) and displayed on the LCD panel 111. Then, the processing returns to step 112.

Therefore, if the time corresponding to the exercise-time information input at step 104 had not elapsed and the exercise amount had not reached the predetermined exercise amount calculated at step 106, the processing corresponding to steps 112 to 117 is repeated. While the processing is repeated, the accumulated amount of the exercise done by the exerciser is calculated, and a message appropriate for the state of the exerciser is selected from among the messages (1) to (5) and displayed on the LCD panel 11.

When the time corresponding to the exercise-time information input at step 104 elapses while the processing corresponding to steps 112 to 117 is repeated, it is determined that the above-described time elapsed, at step 112. As a result, the processing advances from step 112 to step 121 where it is determined whether or not the accumulated exercise amount calculated at step 116 reaches the predetermined exercise amount calculated at step 106.

If the accumulated exercise amount reaches the predetermined exercise amount, the processing advances from step 121 to step 122 where the exercise result is evaluated. The details on the evaluation are displayed on the LCD panel 11, as shown in FIG. 5A, for example, at step 123. Then, at step 124, the routine 100 is finished.

However, when the determination result obtained at step 121 does not show that the accumulated exercise amount reaches the predetermined exercise amount, the processing advances from step 121 to step 131 where the result of the exercise that had been performed until then is evaluated. At step 132, details on the evaluation are displayed on the LCD panel 11, as shown in FIG. 5B, for example.

Then, the processing advances to step 135 where the generation device 10 waits till an instruction is issued, the instruction relating to whether or not the exercise should be continued. If the instruction indicates that the exercise should be continued, the processing returns from step 135 to step 111 so that the processing corresponding to steps 112 to 117 is repeated again. Further, if the instruction does not indicate that the exercise should be continued, at step 135, the processing advances from step 135 to step 136 where the routine 100 is terminated.

When the exercise amount corresponding to the predetermined exercise-amount information input at step 104 is attained while the processing corresponding to steps 112 to 117 is repeated, it is determined that the above-described exercise amount is attained, at step 113. As a result of the determination, the processing advances from step 113 to step 133 where the result of the exercise that had been done until then is evaluated. Then, at step 134, details on the evaluation are displayed on the LCD panel 11, as shown in FIG. 5C, for example.

Then, the processing advances to step 135 where the generation device 10 waits till an instruction is issued, the instruction relating to whether not the exercise should be continued. If the instruction indicates that the exercise should be continued, the processing returns from step 135 to step 111 so that the processing corresponding to steps 112 to 117 is repeated again. Further, if the instruction does not indicate that the exercise should be continued, at step 135, the processing advances from step 135 to step 136 where the routine 100 is terminated.

[4] Example Method for Calculating Exercise Amount

The exercise amount may be calculated according to various methods including a method performed by using metabolic equivalents (METS), for example. In that case, METS denotes an index showing how many times is the amount of oxygen consumed during the exercise larger than that consumed during resting. Further, the index METS denotes the exercise intensity. Namely, the index METS can be shown by the following expressions:

$$METS = \text{oxygen-intake amount during the exercising time}/$$
$$\text{oxygen-intake amount during the resting time}$$
$$= (R + H + V)/R$$

$R$: oxygen-intake amount during the resting time=3.5 [ml/kg·min]

H: horizontal-movement element

V: vertical-movement element

Further, for example, the following expressions hold.

$H = 0.1 \times$ velocity [m/min] during the walking time $H = 0.2 \times$ velocity [m/min] during the running time $V = 0.9 \times$ velocity [m/min] $\times$ inclination [rad]

Therefore, when the exerciser walks at a speed of five kilometers per an hour, the following expressions hold.

$$H = 0.1 \times 5000/60 \text{ [m/min]}$$
$$= 8.33 \text{ [m/min]}$$
$$V = 0.9 \times 5000/60 \text{ [m/min]} \times 0$$
$$= 0$$

Subsequently, the value of METS in the above-described embodiment can be expressed by the following expressions:

$$METS = (3.5 + 8.33 + 0)/3.5$$
$$= 3.38.$$

Next, the exercise amount, that is, the energy-consumption amount can be expressed, as below.

energy-consumption amount [kcal]=weight [kg]×exercise time [h]×METS value

For example, when a person weighing sixty kilograms walks over thirty minutes at a speed of five kilometers per an hour, the following expressions hold.

$$\text{energy-consumption amount [kcal]} = 60 \text{ [kg]} \times 0.5 \text{ [h]} \times 3.38$$
$$= 101 \text{ [kcal]}$$

Further, the fat-burning amount can be expressed, as below. calories necessary for burning one gram of fat=7700 [cal] Therefore, the following expression holds.

$$\text{fat-burning amount [g]} = \text{energy consumption [cal]}/7700 \text{ [cal]}$$

When the above-described values are obtained, the following expressions hold.

$$\text{fat-burning amount [g]} = 101 \text{ [cal]}/7700 \text{ [cal]}$$
$$= 13.1 \text{ [g]}$$

Further, there are relationships that can be expressed by the following expressions:

$$\text{step [cm]} = \text{height [cm]} \times 0.45$$

$$\text{walk distance [cm]} = \text{step [cm]} \times \text{step number.}$$

Therefore, when a person who is 170 cm in height walks over thirty minutes to a track of which tempo is fixed at 120 beats per minute (BPM), the walk distance can be expressed by the following expressions:

$$\text{walk distance} = 170 \text{ [cm]} \times 0.45 \times 120 \text{ [time]}/$$
$$60 \text{ [sec]} \times 30 \text{ [min]} \times 60 \text{ [sec]}$$
$$= 2.754 \text{ [km]}.$$

The above-described numerical values can be displayed, as the exercise result, as shown in FIG. 5A.

Further, the exercise tempo can be determined not only by using the data input at step 104, but also the tempo data detected by the exercise-information sensor 31. In the latter case, the actual exercise amount can be obtained with precision. If the exercise tempo changes, as is the case with FIGS. 7B to 7D, for example, the actual exercise amount can be calculated by obtaining the METS value and the walk-distance amount every time the unit time ΔT elapses and adding the obtained METS values and walk-distance amounts to one another.

[5] Example Data in Exercise-Tempo Changing Mode

Figure 7A:
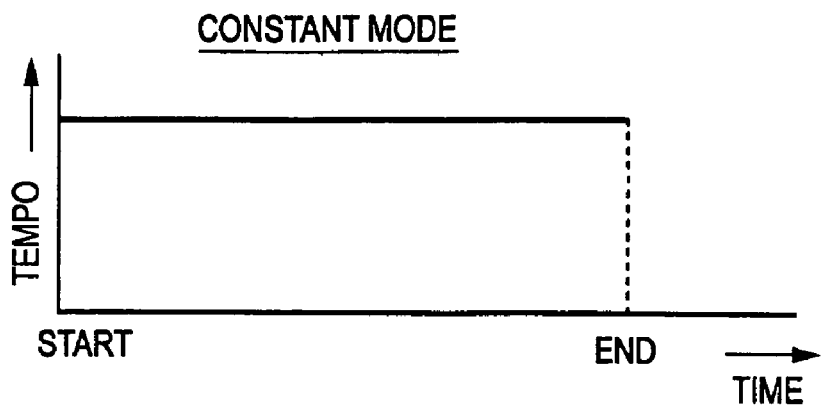
FIG. 7A shows an example exercise mode.
Figure 7B:
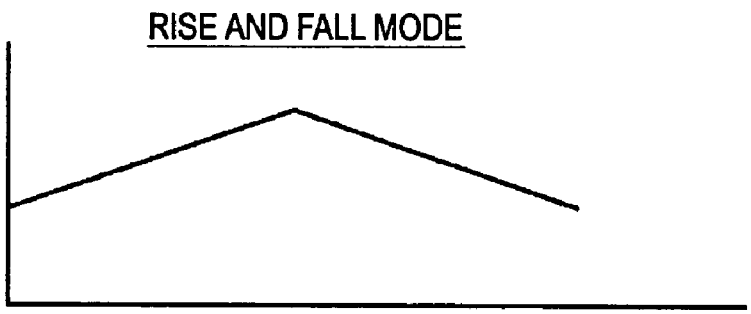
FIG. 7B shows another example exercise mode.
Figure 7C:
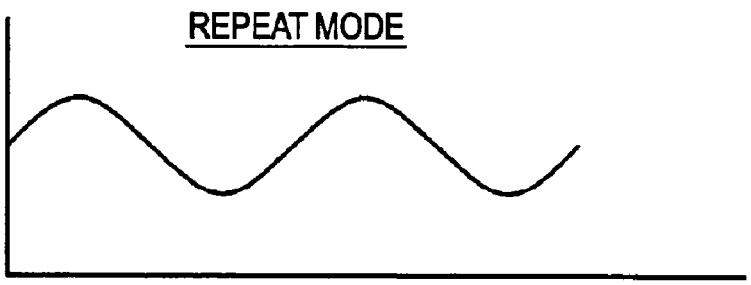
FIG. 7C shows another example exercise mode.

The exercise tempo rises and falls in the exercise mode shown in FIG. 7B. Actually, the above-described mode, that is, the rise-and-fall mode can be achieved by using the tempo information, the exercise-time information, the track-genre information, the tone information, the track-number information in combination, as shown in FIG. 9A.

Namely, FIG. 9A shows the case where the exercise time is determined to be sixty minutes. More specifically, for the first five minutes, the tempo is determined to be 80 BPM, the track genre is determined to be pop, the track tone is determined to be slow, and the track number is determined to be one. For the following ten minutes, the tempo is determined to be 100 BPM, the track genre is determined to be pop, the track tone is determined to be gentle, and the track number is determined to be two. The above-described determination is made also for the following thirty minutes, for example.

Figure 7D:
FIG. 7D shows another example exercise mode.

FIG. 7D shows the case where random mode is selected, as the exercise mode. When the random mode is selected, information items can be used in combination, as shown in FIG. 9B. Namely, for the first ten minutes, the tempo is determined to be 80 BPM, the track genre is determined to be pop, the track tone is determined to be slow, and the track number is determined to be one. For the following ten minutes, the tempo is determined to be 130 BPM, the track genre is determined to be rock, the track tone is determined to be bright, and the track number is determined to be two. The above-described determination is made also for the following ten minutes, for example.

In either of the above-described exercise modes, the expression ΔT=one minute holds, for example. Further, the METS value and the walk-distance value are calculated every time the unit time ΔT elapses, and the calculation results are added up so that the total exercise amount (the energy consumption) or the like is calculated.

[6] Example Track-Generation Method

When composing, a parameter file is prepared so that track data can be generated on the basis of details on the parameter file. FIG. 10 shows an example parameter file used for generating the track data. In that case, the track genre is determined to be pop. The parameter file is prepared in the ROM 22 and interpreted by the CPU 21. Then, data necessary for generating the track data is transmitted to the track-data generation circuit 33.

Therefore, the parameter file stores information about instruments, rhythm, chord progression, performance style, and performance rule. Further, if the exercise tempo is determined to be 120 BPM, the exercise time is determined to be thirty minutes, the track tone is determined to be bright and rhythmical, the track genre is determined to be pop, and the track number is determined to be one, as the composition conditions, data on a predetermined track is generated over thirty minutes, where the rhythm thereof is determined to be sixteen beats, the chord progression is determined to be C-F-G-C of a major chord (bright), chord-only performance, the rhythm is emphasized (rhythmical), and the tempo is determined to be 120 BPM.

[7] Summary

The above-described generation device 10 allows the exerciser to do an exercise including walking, jogging, and so forth to the track, where the tempo of the track used for the exercise is set by the exerciser and the tone and/or genre of the track is determined according to the preference of the exerciser. Further, the generation device 10 can be carried and used by the exerciser through simple operations when the exerciser does the exercise including walking, jogging, and so forth.

Therefore, the user can keep on doing an exercise and continue doing the exercise over a certain period of time. Further, since the track used for the exercise is automatically generated, the user does not have to collect favorite tracks from a CD or the like without concern for copyrights or the like.

[8] Other Embodiments

According to the above-described embodiments, the CPU 21 transmits the data necessary for generating the track data to the track-data generation circuit 33, and the track-data generation circuit 33 automatically generates the track data according to the transmitted necessary data. As for the tempo and/or time of the track, however, the CPU 21 may control the track-data generation circuit 33 in real time, so as to attain a desired tempo and/or time.

Further, according to the above-described embodiments, the track tempo is determined according to the speed-and-tempo information input by the user. However, it is also possible to generate data on a track of which tempo is determined according to tempo information detected by the exercise-information sensor 31. Further, it is also possible to calculate the exercise amount according to the tempo information detected by the exercise-information sensor 31. Further, if an integer ratio stands between the track tempo and the tempo of an exercise done by the user, the exercise can be done. Therefore, it may be determined that the integer ratio stands between the track tempo and the tempo of the exercise done by the user.

Further, the user's body information may include information about the age, birthday, sex, step and so forth of the user in addition to the information about the height and weight of the user. Further, the parameter file shown in FIG. 10 may be prepared in a purpose-built storage device.

Further, the track information, the exercise-amount information, and the user's body information obtained when the user does the exercise may be stored, as historical data. The historical data can be retrieved, as required, so as to aid in managing the exercise amount. Further, the track-data generation circuit 33 may store and reuse the track data generated by the track-data generation circuit 33. The generated track data may be stored in a predetermined storage device including an optical disk, a magneto-optical disk, a magnetic tape, a hard disk, a semiconductor memory, an integrated-circuit (IC) card, and so forth.

It should be understood by those skilled in the art that various modifications, combinations, sub-combinations and alterations may occur depending on design requirements and other factors insofar as they are within the scope of the appended claims or the equivalents thereof.

What is claimed is:

1. An audio-signal generation device comprising:
a generation circuit which generates audio track data for providing a continuous audio signal representative of at least one musical track;
input means which receives information input by a user;
an exercise-information sensor for detecting a motion of the user's body; and
an analysis circuit for analyzing in real time, information transmitted from the exercise-information sensor;
wherein the generation circuit generates the audio track data on the basis of information about the user's body, information about an exercise to be done, and information about a characteristic of an audio track to which the user listens during the exercise that are input via the input means.

2. The audio-signal generation device according to claim 1, wherein the exercise information input via the input means indicates at least one of a tempo of the exercise, a time of the exercise, and a type of the exercise.

3. The audio-signal generation device according to claim 1, wherein the track-characteristic information input via the input means includes at least one of rhythm information, genre information, chord-progression information, tonality information, track-number information, repeat-number information, and a combination of at least two of the rhythm information, the genre information, the chord-progression information, the tonality information, the track-number information, and the repeat-number information.

4. The audio-signal generation device according to claim 1, wherein the user's-body information input via the input means includes at least one of height information, weight information, age information, sex information, and step information.

5. The audio-signal generation device according to claim 1, further comprising:
calculation means which calculates an amount of the exercise when the user does the exercise to track data performed on the basis of the audio track data generated by the generation circuit; and
output means which outputs information about the exercise amount calculated by the calculation means, as exercise-amount information.

6. The audio-signal generation device according to claim 5, wherein the exercise-amount information indicates at least one of an exercise time, an exercise intensity, an exercise amount, a calorie consumption, and a fat-burning amount.

7. The audio-signal generation device according to claim 6, further comprising storage means storing at least one of the track information, the exercise-amount information, and the information about the user's body.

8. The audio-signal generation device according to claim 7, wherein the storage means includes at least one of an optical disk, a magneto-optical disk, a magnetic tape, a hard disk, a semiconductor memory, and an integrated-circuit card.

9. An audio-signal generation device comprising:
a generation circuit which generates audio track data for providing a continuous audio signal representative of at least one musical track;
an input unit which receives information input by a user;
an exercise-information sensor for detecting a motion of the user's body; and
an analysis circuit for analyzing in real time, information transmitted from the exercise-information sensor;
wherein the generation circuit generates the audio track data on the basis of information about the user's body, information about an exercise to be done, and information about a characteristic of an audio track to which the user listens during the exercise that are input via the input unit.

* * * * *